(12) United States Patent
Hattori et al.

(10) Patent No.: US 9,238,662 B2
(45) Date of Patent: Jan. 19, 2016

(54) SILICONE COMPOUND HAVING A RADICAL-POLYMERIZABLE GROUP AND A METHOD FOR THE PREPARATION THEREOF

(71) Applicant: SHIN-ETSU CHEMICAL CO., LTD., Tokyo (JP)

(72) Inventors: Hatsuhiko Hattori, Annaka (JP); Shoji Ichinohe, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/484,879

(22) Filed: Sep. 12, 2014

(65) Prior Publication Data

US 2015/0087853 A1    Mar. 26, 2015

(30) Foreign Application Priority Data

Sep. 25, 2013    (JP) ................................ 2013-198208

(51) Int. Cl.
| | |
|---|---|
| *C07F 7/00* | (2006.01) |
| *C07F 7/02* | (2006.01) |
| *C08G 77/20* | (2006.01) |
| *C08G 77/26* | (2006.01) |
| *G02B 1/04* | (2006.01) |
| *C08F 230/08* | (2006.01) |

(52) U.S. Cl.
CPC ................ *C07F 7/025* (2013.01); *C08G 77/20* (2013.01); *C08G 77/26* (2013.01); *C08F 230/08* (2013.01); *G02B 1/043* (2013.01)

(58) Field of Classification Search
CPC ......... C07F 7/025; C08L 83/04; C08G 77/20; G02B 1/043
USPC ........................................................ 556/424
See application file for complete search history.

(56) References Cited

U.S. PATENT DOCUMENTS

| 3,808,178 | A | 4/1974 | Gaylord | |
|---|---|---|---|---|
| 2005/0176911 | A1 | 8/2005 | Zanini et al. | |
| 2007/0161810 | A1* | 7/2007 | Schorzman | C08G 77/388 556/418 |
| 2011/0206936 | A1* | 8/2011 | Maliverney et al. | 428/447 |

FOREIGN PATENT DOCUMENTS

| JP | A-2007-186709 | 7/2007 |
|---|---|---|
| JP | A-2007-526364 | 9/2007 |
| WO | 2010/071691 A1 | 6/2010 |
| WO | WO 2012/130956 A1 | 10/2012 |

OTHER PUBLICATIONS

Akiyoshi et al., "Contact Lens Materials," *Encyclopedia of Advanced Biomaterials*, Jun. 2012, Chapter 5, pp. 528-533 (with partial translation).

* cited by examiner

*Primary Examiner* — Porfirio Nazario Gonzalez
*Assistant Examiner* — Kofi Adzamli
(74) *Attorney, Agent, or Firm* — Oliff PLC

(57) ABSTRACT

A purpose of the present invention is to provide a polymerizable group-containing silicone compound which is liquid at room temperature, has good handling properties and compatibility with other polymerizable monomers. The present invention provides a silicone compound represented by the general formula (1) which has a structure represented by the following formula (2) or (3):

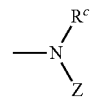

(2)

wherein $R^c$ is an alkyl group having 1 to 10 carbon atoms and Z is a radical-polymerizable group;

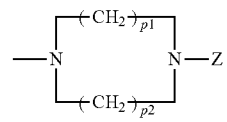

(3)

wherein $p^1$ and $p^2$ are, independently of each other, positive integers such that a total number of $p^1$ and $p^2$ is 3 to 10, and Z is a radical-polymerizable group;
and has a silicone structure bonded to the aforesaid formula (2) or (3) via a substituted or unsubstituted divalent hydrocarbon group having 1 to 10 carbon atoms. The present invention further provides a method for preparation the aforesaid silicone compound.

12 Claims, 2 Drawing Sheets

SILICONE COMPOUND HAVING A RADICAL-POLYMERIZABLE GROUP AND A METHOD FOR THE PREPARATION THEREOF

CROSS REFERENCE

This application claims the benefits of Japanese Patent application No. 2013-198208 filed on Sep. 25, 2013, the contents of which are hereby incorporated by reference.

FIELD OF THE INVENTION

The present invention relates to a silicone compound having a radical-polymerizable group at the terminal and a method for the preparation of the silicone compound. Specifically, the present silicone compound is liquid at room temperature.

Silicone hydrogels for contact lens materials were developed. Encyclopedia of Advanced Biomaterials, Non-Patent Literature 1, describes that a silicone compound such as polydimethylsiloxane, which has a polymerizable group, is as a raw material to improve oxygen permeability, flexibility and mechanical strength of lenses. U.S. Pat. No. 3,808,178 describes 3-[tris(trimethylsiloxy)silyl]propyl methacrylate (TRIS) as a silicone monomer used for ophthalmic devices. A silicone hydrogel is prepared by copolymerization of a hydrophilic monomer and a polymerizable silicone compound. Therefore, it is important that a polymerizable silicone compound is compatible with a hydrophilic monomer. However, TRIS has poor compatibility with a hydrophilic monomer. Non-patent literature 1, Japanese Patent Application Laid-Open No. 2007-186709 and Japanese National Phase Publication No. 2007-526364 describe a method for improving compatibility of a polymerizable silicone compound with a hydrophilic monomer by introducing a polar functional group such as an amide, urethane or hydroxyl group into the polymerizable silicone compound.

WO2012/130956 describes a composition for preparing an ophthalmic lens, comprising units derived from 3-[tris(trimethylsiloxy)silyl]propyl acrylamide. 3-[tris(trimethylsiloxy)silyl]propyl acrylamide is often used as one of monomer components for contact lens materials because of its good UV curability.

PRIOR LITERATURES

Patent Literature 1: U.S. Pat. No. 3,808,178
Patent Literature 2: WO2012/130956
Patent Literature 3: Japanese Patent Application Laid-Open No. 2007-186709
Patent Literature 4: Japanese National Phase Publication No. 2007-526364
Non-Patent Literature 1: Encyclopedia of Advanced Biomaterials, Akiyoshi et. al., published in June, 2012, Chapter V, Paragraph V, pages 528-533, "CONTACT LENS MATERIALS"

SUMMARY OF THE INVENTION

However, 3-[tris(trimethylsiloxy)silyl]propyl acrylamide has a melting point of approximately 50 degrees C. and is solid at room temperature, so that the handling properties of the compound is bad at room temperature. Further, the compound sometimes has poor compatibility with other polymerizable monomers.

One of the purposes of the present invention is to provide a polymerizable group-containing silicone compound which is liquid and has good handling properties at room temperature and has excellent compatibility with other polymerizable monomers.

The inventors have found a silicone compound in which a radical-polymerizable group is introduced via an —NH— group at the terminal and the hydrogen atom bonded to the nitrogen atom is substituted with an alkyl group, and that this silicone compound is liquid at room temperature and has good handling properties.

Thus, the present invention provides a silicone compound represented by the following general formula (1):

(1)

wherein $R^1$, $R^2$ and $R^3$ are, independently of each other, represented by the following formula (a):

(a)

wherein R is, independently of each other, a monovalent hydrocarbon group having 1 to 10 carbon atoms and n is an integer of from 0 to 20;

A is represented by the following formula (2) or (3):

(2)

wherein $R^c$ is an alkyl group having 1 to 10 carbon atoms, and Z is a radical-polymerizable group;

(3)

wherein $p^1$ and $p^2$ are, independently of each other, positive integers such that a total number of $p^1$ and $p^2$ is 3 to 10, and Z is a radical-polymerizable group; and Q is a substituted or unsubstituted divalent hydrocarbon group having 1 to 10 carbon atoms.

Further, the present invention provides a method for preparing the silicone compound.

The present silicone compound has a low melting point and is liquid at room temperature, so that the silicone compound has good handling properties. Further, the silicone compound has good compatibility with other monomer components.

DETAILED DESCRIPTION OF THE INVENTION

Figure 1:
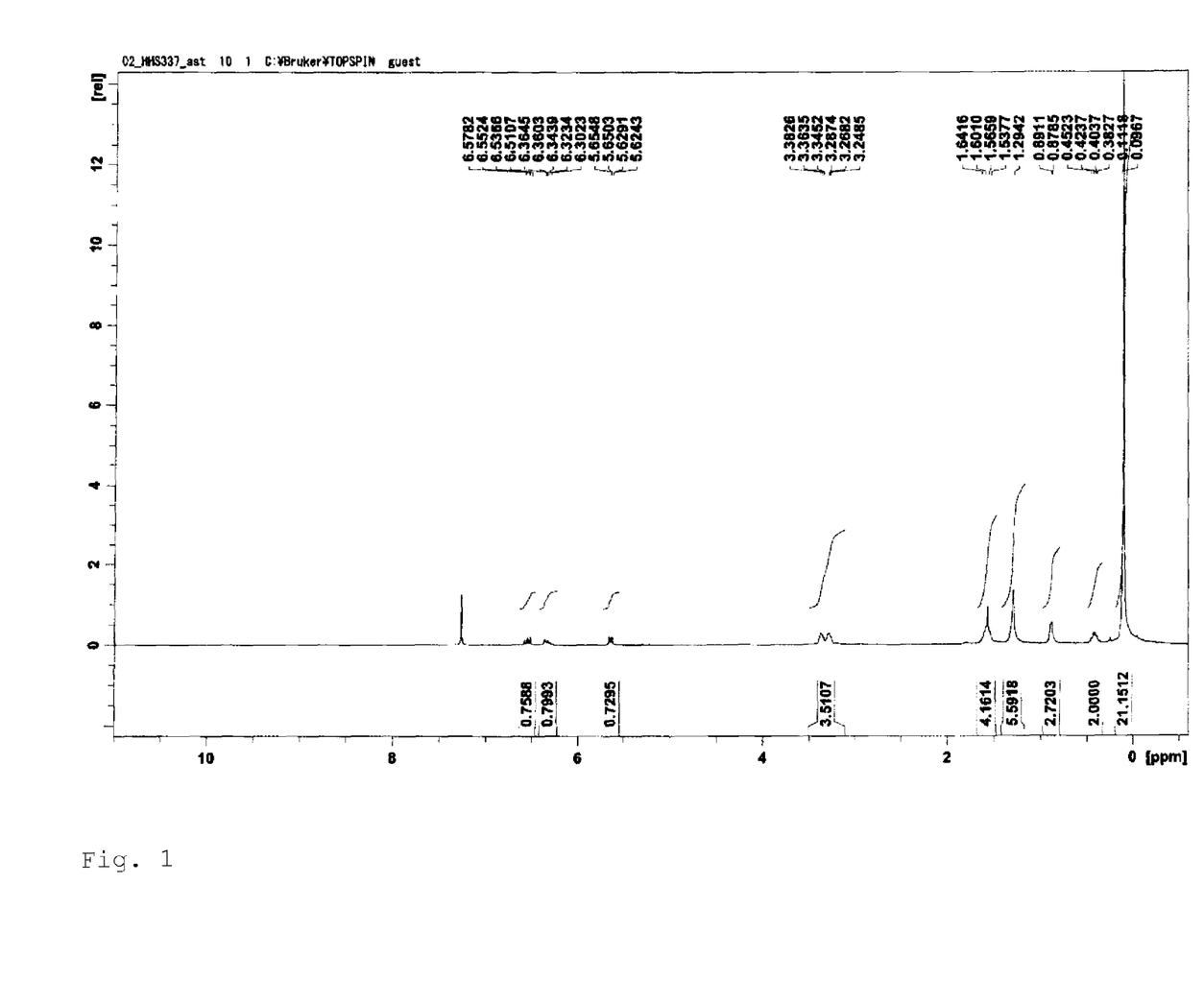
FIG. 1 is a chart of $^1$H-NMR spectra of the silicone compound prepared in Example 1.
Figure 2:
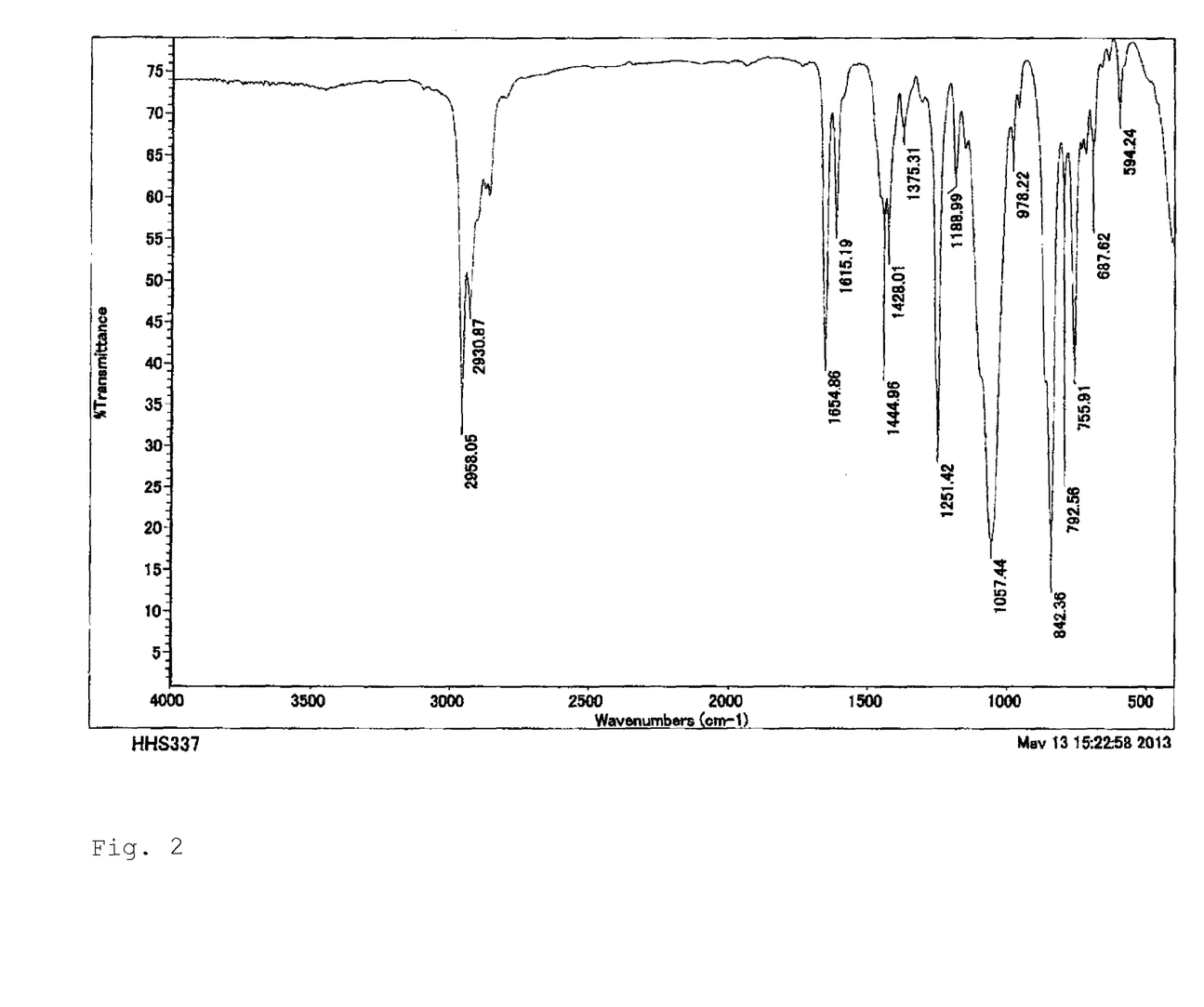
FIG. 2 is a chart of IR spectra of the silicone compound prepared in Example 1.

The present invention will be described below in detail.

In the aforesaid formula (1), $R^1$, $R^2$ and $R^3$ are, independently of each other, represented by the following formula (a):

(a)

In the formula (a), R is, independently of each other, a substituted or unsubstituted monovalent hydrocarbon group having 1 to 10 carbon atoms, preferably 1 to 8 carbon atoms. Examples of the monovalent hydrocarbon group include alkyl groups such as a methyl group, an ethyl group, a propyl group, a butyl group, a pentyl group, a hexyl group, a hepty group, an octyl group, a nonyl group and a decyl group; cycloalkyl groups such as a cyclopentyl group and a cyclohexyl group; aryl groups such as a phenyl group and a tolyl group; and alkenyl groups such as a vinyl group and an allyl group; and these groups where a part or the whole of their hydrogen atoms bonding to carbon atoms are replaced with a halogen atom(s), such as a chlorine atom and a fluorine atom, such as, for instance, halogen-substituted alkyl groups and halogen-substituted alkenyl groups. Among these, alkyl groups such as a methyl group, an ethyl group, a propyl group and a butyl group are preferred. In particular, a methyl group is preferred.

In the formula (a), n is an integer of from 0 to 20, preferably from 0 to 10 and, in particularly, 0. $R^1$, $R^2$ and $R^3$ may be different from each other. It is preferred that all of $R^1$, $R^2$ and $R^3$ have the same value of n. In particular, all of $R^1$, $R^2$ and $R^3$ are the following group:

In the aforesaid formula (1), Q is a substituted or unsubstituted divalent hydrocarbon group having 1 to 10 carbon atoms. Examples of the divalent hydrocarbon group include groups such as an ethylene group, a 1,3-propylene group, a 1-methylpropylene group, a 1,1-dimethylpropylene group, a 2-methylpropylene group, a 1,2-dimethylpropylene group, a 1,1,2-trimethylpropylene group, a 1,4-butylene group, a 2-methyl-1,4-butylene group, a 2,2-dimethyl-1,4-butylene group, a 3-methyl-1,4-butylene group, a 2,3-dimethyl-1,4-butylene group, a 2,2,3-trimethyl-1,4-butylene group, a 1,5-pentylene group, a 1,6-hexanylene group, a 1,7-heptanylene group, a 1,8-octanylene group, a 1,9-nonanylene group and a 1,10-decanylene group, and these groups where a part or the whole of their hydrogen atoms bonding to carbon atoms are replaced with a halogen atom(s) such as a chlorine atom and a fluorine atom, such as halogen-substituted alkylene groups. Among these, a propylene group, a 2-methylpropylene group, a 1,4-butylene group and a 3-methyl-1,4-butylene group are preferable and a 1,3-propylene group is most preferable.

In the aforesaid formula (1), A is represented by the following formula (2) or (3):

(2)

(3)

wherein, $R^c$ is an alkyl group having 1 to 10 carbon atoms, $p^1$ and $p^2$ are, independently of each other, positive integers such that a total number of $p^1$ and $p^2$ is 3 to 10, and Z is a radical-polymerizable group.

In the aforesaid formula (2), $R^c$ is preferably an alkyl group having 4 to 7 carbon atoms. The alkyl group may have any linear, branched, or cyclic structure. Examples of the alkyl group include a methyl group, an ethyl group, a propyl group, a n-butyl group, a s-butyl group, a t-butyl group, an i-butyl group, a n-pentyl group, a n-hexyl group, a n-heptyl group, a n-octyl group, a n-nonyl group, a n-decanyl group, a cyclopentyl group, a cyclohexyl group, a cycloheptyl group, a cyclooctyl group, a cyclononyl group and a cyclodecanyl group. Among these, a n-butyl group, a n-hexyl group, a cyclopentyl group and a cyclohexyl group are preferable in view of easy availability and good handling properties.

The group represented by the aforesaid formula (3) has a divalent cyclic diaza structure. $p^1$ and $p^2$ are, independently of each other, positive integers such that a total number of $p^1$ and $p^2$ is 3 to 10. Examples of the group include structures such as imidazolidinylene, piperazinylene, 1,4-diazacycloheptanylene, 1,4-diazacyclooctanylene, 1,4-diazacyclononanylene and 1,5-diazacyclodecanylene. Among these, a piperazinylene structure is preferable, in view of easy availability.

Examples of the group represented by the formula (1) include the following compound.

wherein A is a group selected from the following formulas:

and wherein $R^c$ is a butyl group, a n-hexyl group or a cyclohexyl group and Z is a radical-polymerizable group.

In the present silicone compound, the radical-polymerizable group represented by the aforesaid Z is, for instance, an acryl group, a methacryl group, an alkynyl group, a styryl group, an indenyl group, an alkenyl group, a cycloalkenyl group or a norbornyl group, or a conjugated or disconjugated alkadiene group. These groups have a hetero atom which bonds to a nitrogen atom and may have a substituent group having 1 to 10 carbon atoms and a linear, branched or cyclic structure. Among these, an acryl group and a methacryl group are preferable because their reactions can be carried out easily.

The present invention further provides a method for the preparation of the silicone compound represented by the aforesaid formula (1).

The present method comprises a step of reacting a compound represented by the following formula (9):

(4)

wherein $R^1$, $R^2$, $R^3$ and Q are as defined above, X is a group selected from the group consisting of a chlorine atom, a bromine atom, a bromanyl group, an iodine atom, an iodanyl group, a mesyl group, a tosyl group, a trifluoromethanesulfonyl group, a nosyl group and an epoxy group;
with a compound represented by the following formula (5) or (6):

$R^c - NH_2$ (5)

(6)

wherein $R^c$, $p^1$ and $p^2$ are as defined above;
in a polar solvent and in the presence of a base and a reaction promoter to prepare a precursor compound represented by the following formula (1'):

(1')

wherein $R^1$, $R^2$, $R^3$ and Q are as defined above and A' is represented by the following formula (2') or (3'):

(2')

(3')

wherein $R^c$, $p^1$ and $p^2$ are as defined above;
and subsequently a step of reacting said precursor compound represented by the aforesaid formula (1') with a compound having a radical-polymerizable group to prepare the silicone compound represented by the aforesaid formula (1).

In the formula (4), X is a group selected from the group consisting of a chlorine atom, a bromine atom, a bromanyl group, an iodine atom, an iodanyl group, a mesyl group, a tosyl group, a trifluoromethanesulfonyl group, a nosyl group and an epoxy group. Among these, a chlorine atom is preferable owing to its easy availability.

The compound represented by the aforesaid formula (5) is an alkyl amine. Examples of the alkyl amine include ethyl amine, propyl amine, n-butyl amine, s-butyl amine, t-butyl amine, i-butyl amine, n-pentyl amine, n-hexyl amine, n-heptyl amine, n-octyl amine, n-nonyl amine, n-decanyl amine, cyclopentyl amine, cyclohexyl amine, cycloheptyl amine, cyclooctyl amine, cyclononyl amine and cyclo decanyl amine. Among these, n-butyl amine, n-hexyl amine, cycloheptyl amine and cyclohexyl amine are preferable owing to their easy availability and easy handling properties.

The compound represented by the aforesaid formula (6) has a cyclic diaza structure. Examples of the compound include an imidazolidine, piperazine, 1,4-diazacycloheptane, 1,4-diazacyclooctane, 1,4-diazacyclononane and 1,5-diazacyclodecane. Among these, piperazine is particularly preferable owing to its availability.

The present method first comprises a step of reacting the compound represented by the aforesaid formula (4) and the compound represented by the aforesaid formula (5) or (6) in a polar solvent and in the presence of a base and a reaction promoter to prepare a precursor compound represented by the aforesaid formula (1'). In this step, examples of the base include alkali metal salts, alkaline earth metal salts and tertiary amine compounds.

Examples of the alkali metal salts include lithium hydride, lithium hydroxide, lithium carbonate, lithium hydrogen carbonate, lithium aluminum hydride, lithium borohydride, methyl lithium, butyl lithium, phenyl lithium, sodium hydride, sodium hydroxide, sodium carbonate, sodium hydrogen carbonate, sodium borohydride, potassium hydride, potassium hydroxide, potassium carbonate, potassium hydrogen carbonate and dipotassium hydrogenphosphate.

Examples of the alkaline earth metal salts include magnesium hydroxide, magnesium carbonate, calcium hydroxide, calcium carbonate, strontium hydroxide, strontium carbonate, barium hydroxide and barium carbonate.

Examples of the tertiary amine compounds include trimethylamine, triethylamine, i.e. $Et_3N$, diisopropylethylamine, i.e. DIPEA, tri-n-butylamine, tri-n-pentylamine, tri-n-hexylamine, tri-n-heptylamine, tri-n-octylamine, N-methylpyrrolidine, N-methylpiperazine, N-methylmorpholine, N,N,N', N'-tetramethylethylenediamine, i.e. TMEDA, N-methylimidazole, i.e. NMI, pyridine, 2,6-lutidine, 1,3,5-collidine, N,N-dimethylaminopyridine, pyrazine, quinoline, 1,8-diazabicyclo[5,4,0]undec-7-ene, i.e. DBU, and 1,4-diazabicyclo[2,2,2]octane, i.e. DABCO.

Among the aforesaid bases, sodium carbonate, potassium carbonate, triethyl amine and pyridine are preferable in view of their reactivity. In particularly, pyridine is preferable. The amount of the base is preferably the same molar amount or more with a molar amount of the compound represented by the aforesaid formula (5) or (6). The amount of the base is further preferably the same molar amount of that of the compound represented by the aforesaid formula (5) or (6).

Examples of the reaction promoter include lithium bromide, lithium iodide, sodium bromide, sodium iodide; quaternary alkylammonium bromides such as tetramethylammonium bromide, tetraethylammonium bromide and tetrabuthylammonium bromide; quaternary alkylammonium iodides such as tetramethylammonium iodide, tetraethylammonium iodide and tetrabuthylammonium iodide; potassium bromide and potassium iodide. Among these, potassium iodide is preferable in view of promotion of the reaction. The amount of the reaction promoter is preferably 1.0 mole or less, particularly 0.5 mole or less, relative to 100 moles of the compound represented by the aforesaid general formula (4). If the amount of the reaction promoter is too much, coloration may occur during a reaction.

U.S. Pat. No. 3,719,697 describes a method for preparing the compound represented by the aforesaid formula (1') in the presence of the nonpolar solvent. However, the reaction rate in this method is slow. This is because, as the reaction proceeds, in the presence of the nonpolar solvent such as hydrocarbon solvents such as pentane, hexane, heptane, cyclohexane, toluene and xylene, phase separation occurs between a phase of the hydrocarbon solvent containing the compound represented by the formula (1') and the compound represented by the formula (4) and a phase containing abase and the compound represented by the formula (5) or (6) and, then, the reaction does not proceed any more even though some of the compound represented by the formula (4) is still unreacted. Therefore, in the present invention, the preparation of the precursor compound is conducted in the presence of a polar solvent.

Further, among the polar solvents, alcohol solvents such as methanol and ethanol react with the compound represented by the formula (5) or (6) to provide a small amount of ether compounds as a by-product, though the alcohol solvents have a low reactivity with the compound represented by the formula (4). Therefore, the polar solvent used in the present method is preferably selected from amide compounds, ether compounds, keton compounds, alkyl nitrile compounds and halogenated hydrocarbon compounds. In particular, preferred are amide compounds which may have a linear, branched or cyclic hydrocarbon group having 1 to 8 carbon atoms on the nitrogen atom; ether compounds which have a linear, branched or cyclic structure, may have an unsaturated bond, and have 1 to 8 carbon atoms and 1 to 3 oxygen atoms; keton compounds which have 1 to 7 carbon atoms and a linear, branched or cyclic structure; alkyl nitrile compounds having a linear, branched or cyclic structure and 1 to 6 carbon atoms; and substituted or unsubstituted halogenated hydrocarbon compounds having a linear, branched or cyclic structure and 1 to 10 carbon atoms.

Specifically, examples of the aforesaid polar solvent include N,N-Dimethylformamide, i.e. DMF, N,N'-dimethylacetamide, i.e. DMAc, 1,3-dimethyl-2-imidazolidinone, i.e. DMI, 1,3-Dimethyl-3,4,5,6-tetrahydro-2(1H)-pyrimidinone, i.e. DMPU, diethylether, t-butylmethylether, i.e. TBME, dibutyl ether, cyclopentyl methyl ether, i.e. CPME, diphenyl ether, dimethoxymethane, i.e. DMM, 1,2-dimethoxyethane, diethyleneglycol dimethyl ether, tetrahydrofuran, i.e. THF, tetrahydropyran, i.e. THP, 4-methylpyran, dioxane, 2-methyltetrahydrofuran, 2-ethyltetrahydrofuran, acetone, methyl ethyl ketone, i.e. MEK, methyl isobutyl ketone, i.e. MIBK, cyclopentanone, cyclohexanone, cycloheptanone, acetonitrile, propionitrile, butyronitrile, a,a,a-trifluoromethylbenzene, chlorobenzene, chloroform, dichloromethane and 1,2-dichloroethane. Among these, in view of a boiling point, an influence on environment and a purity of a product obtained, preferred are DMAc, DMI, DMPU, CPME, diphenylether, 1,2-dimethoxyethane, diethyleneglycol dimethylether, 2-ethyl tetrahydrofuran, MIBK, propionitrile, butyronitrile, a,a,a-trifluoromethyl benzene and chlorobenzene. DMAc is the most preferred. The amount of the polar solvent is 0.5 to 2.0 moles, preferable 1.0 mole, per mole of the compound represented by the aforesaid formula (4).

For instance, the compound represented by the aforesaid formula (4), the compound represented by the aforesaid formula (5) or (6), a base, a reaction promoter and a polar solvent are put in a flask and heated to a internal temperature such as 130 degrees C. with stirring. Subsequently, disappearance of a signal, $^1$H-NMR, of $CH_2$ which is next to a chlorine atom of the raw material having siloxane groups, formula (4), is confirmed and, then, the mixture is cooled to room temperature, salts are removed by filtration through a paper filter, low-volatile materials are evaporated at a temperature such as 50 degrees C. under a reduced pressure such as 10 KPa, and the residues are distilled at a temperature such as 140 degrees C. under a reduced pressure such as 0.5 Pa, to obtain the precursor product represented by the aforesaid formula (1'). The heating and stirring temperature and the reduced pressure may be selected according to the conventional manners.

The compound represented by the aforesaid formula (1) is prepared by reacting the precursor compound represented by the aforesaid formula (1') and the compound having a radical-polymerizable group. The radical-polymerizable group is, for instance, an acryl group, a methacryl group, an alkynyl group, a styryl group, an indenyl group, an alkenyl group, a cycloalkenyl group, a norbornyl group or a conjugated or disconjugated alkadiene group. These groups have a hetero atom which may bind to a nitrogen atom and may have a substituent group having 1 to 10 carbon atoms and a linear, branched or cyclic structure. Examples of the compound having the radical-polymerizable group include oxides, halogenides, acid anhydrides and mixed acid esters. These compounds have the aforesaid radical-polymerizable group. Further specifically, (meth)acrylic acid chloride and (meth)acryloxy pivalate may be named. Among these, (meth)acrylic acid chloride is more preferred.

The amount of the aforesaid compound having the radical-polymerizable group is more than 1 mole and at most 2 moles, per mole of the precursor compound represented by the aforesaid formula (1'). If the amount is less than the lower limit, the precursor compound represented by the formula (1') remains in the product obtained. If the amount is more than the upper limit, the reacting solution tends to be acidic and an amount of impurities may increase. The amount is further preferably 1.05 moles or more and at most 1.8 moles, per mole of the precursor compound, in view of costs of the precursor compound.

The reaction of the precursor compound and the radical-polymerizable group-containing compound are preferably carried out in an aqueous solution of an alkali metal salt or an alkaline earth metal salt. Examples of the alkali metal salt include lithium hydroxide, lithium carbonate, lithium hydrogen carbonate, sodium hydride, sodium hydroxide, sodium carbonate, sodium hydrogen carbonate, sodium borohydride, potassium hydride, potassium hydroxide, potassium carbonate, potassium hydrogen carbonate, dipotassium hydrogenphosphate. Examples of the alkaline earth metal salt include magnesium hydroxide, magnesium carbonate, calcium hydroxide, calcium carbonate, strontium hydroxide, strontium carbonate, barium hydroxide and barium carbonate. Among these, sodium carbonate and potassium carbonate are preferred because of their easy availability, good handling properties and an improvement of reactivity, and sodium carbonate is the most preferred. The amount of sodium carbonate is 1 mole or more, further preferably 2 moles or more, per mole of the compound having a radical-polymerizable group in order to maintain an alkaline condition of the reaction solution. Owing to the presence of the sodium carbonate and water, unreacted (meth)acrylic acid chloride and by-produced acrylic acid chloride can be removed easily.

For instance, the precursor compound, the compound having a radical-polymerizable group and a 10% aqueous solution of sodium carbonate are mixed by stirring, the aqueous solution of sodium carbonate is removed from an organic phase and, then, the organic phase is washed with water. Subsequently, the polymerization inhibitor is added to the organic solution and volatile materials are distilled off at a temperature such as 50 degrees C. under a reduced pressure such as 13 KPa to obtain the present silicone compound.

The present silicone compound has a low melting point and liquid at room temperature and, therefore, has good handling properties and good compatibility with other monomer components. The other monomer is not limited to particular one and may be selected from the conventional components depending on the intended use such as these described below. For instance, nitrogen atom-containing monomers such as these N-vinylpyrrolidone, N,N-dimethylacrylamide and N-methyl-3-methylidenepyrrolidone; and hydrophilic monomers such as a methacrylic acid and hydroxyethyl(meth)acrylate may be used.

A composition obtained by mixing the present silicon compound with other monomer is useful for, for instance, ophthalmic device compositions, coating materials or cosmetic compositions. Examples of the cosmetics compositions include skin care cosmetics, hair care cosmetics, antiperspirant cosmetics, deodorant cosmetics, makeup cosmetics and ultraviolet protection cosmetics.

EXAMPLES

The present invention will be explained below in further detail with reference to a series of the Examples and the Comparative Examples, though the present invention is in no way limited by these Examples.

In the following descriptions, molecular structures were determined with nuclear magnetic resonance analysis, $^1$H-NMR, and infrared spectroscopy, IR. The apparatuses were as follows.

$^1$H-NMR: AVANCE III, ex Bruker Biospin Co., Ltd.
IR: NICOLET6700, ex Thermo Fisher Scientific Co., Ltd.

Synthesis Example 1

In a three-necked flask equipped with a thermometer, a stirring device and a nitrogen inflow instrument, were put 1.0 mole of [(CH$_3$)$_3$SiO]$_3$Si(CH$_2$)$_2$Cl, 3.0 moles of n-hexylamine, 0.1 mole of potassium iodide, 3.0 moles of pyridine and 1.0 mole of N,N-dimethylacetamide and, then, heated to an internal temperature of 130 degrees C. with stirring. Disappearance of a signal, $^1$H-NMR, of CH$_2$ which was next to a chlorine atom of the raw material, [(CH$_3$)$_3$SiO]$_3$Si(CH$_2$)$_3$Cl, was confirmed and, then, the mixture was cooled to room temperature, salts were removed by a filtration through a paper filter, low-volatile materials were evaporated at 50 degrees C. and under a reduced pressure of 10 KPa and the residues were distilled at 140 degrees C. to obtain a very pale yellow and transparent product which was oily at room temperature.

A molecular structure of the product obtained was analyzed by $^1$H-NMR and IR to find that the product was a silicone compound represented by the following formula. The yield was 78%.

The $^1$H-NMR spectra and IR spectra are as described below.

$^1$H-NMR (400 MHz, CDCl$_3$): δ 0.10 (s, 27H), 0.42-0.51 (m, 2H), 0.85-0.91 (m, 3H), 1.10-1.58 (m, 10H), 2.60 (t, J=8.2 Hz, 2H)

IR (NaCl): ν 756, 792, 842, 1058, 1251, 1428, 1445, 1655, 2968, 3453.

Synthesis Example 2

The procedures of Synthesis Example 1 were repeated, except that n-buthylamine was used in place of n-hexylamine, to obtain a very pale yellow and transparent product which was oily at room temperature. A molecular structure of the product obtained was analyzed by $^1$H-NMR and IR to find that the product was a silicone compound represented by the following formula. The yield was 76%.

The $^1$H-NMR spectra and IR spectra are as described below.

$^1$H-NMR (400 MHz, CDCl$_3$): δ 0.10 (s, 27H), 0.42-0.51 (m, 2H), 0.85-0.91 (m, 3H), 1.10-1.58 (m, 6H), 2.60 (t, J=8.2 Hz, 2H)

IR (NaCl): ν 757, 789, 843, 1056, 1250, 1427, 1654, 2972, 3452.

Synthesis Example 3

The procedures of Synthesis Example 1 were repeated, except that piperazine was used in place of n-hexylamine, to obtain a very pale yellow and transparent product which was oily at room temperature. The molecular structure of the product obtained was analyzed by $^1$H-NMR and IR to find that the product was a silicone compound represented by the following formula. The yield was 76%.

The ¹H-NMR spectra and IR spectra are as described below.

¹H-NMR (400 MHz, CDCl₃): δ 0.10 (s, 27H), 0.42-0.51 (m, 2H), 1.46-1.58 (m, 2H), 2.23-2.45 (brs, 4H), 2.60-2.92 (m, 6H)

IR (NaCl): ν 759, 785, 845, 1053, 1189, 1251, 1430, 1653, 2983, 3355.

Example 1

In a three-necked flask equipped with a thermometer, a dropping funnel and a nitrogen inflow instrument, and a magnetic stirring bar therein, were put 1.0 mole of the silicone compound prepared in Synthesis Example 1, 1.05 moles of acrylic acid chloride and 2.0 moles of sodium carbonate in an aqueous 10% solution and stirred. Subsequently, the aqueous solution of sodium carbonate was removed from an organic phase and, then, the organic phase was washed with water. A polymerization inhibitor, BHT, was added to the organic phase and volatile materials were distilled off at 50 degrees C. and under a reduced pressure of 13 KPa to obtain a pale yellow and transparent product which was oily at room temperature. A molecular structure of the product obtained was analyzed by ¹H-NMR and IR to find that the product was a silicone compound represented by the following formula. The yield was 91%.

The ¹H-NMR spectra and IR spectra are as described below.

¹H-NMR (400 MHz, CDCl₃): δ 0.09 (s, 27H), 0.35-0.46 (m, 2H), 0.85-0.93 (m, 3H), 1.23-1.36 (m, 6H), 1.12-1.52 (m, 4H), 3.21-3.33 (m, 2H), 3.33-3.40 (m, 2H), 5.63 (dd, J=10.3, 2.0 Hz, 1H), 6.34 (ddd, 16.7, 8.4, 2.0 Hz, 1H), 6.54 (dd, 16.7, 10.3 Hz, 1H)

IR (NaCl): ν 792, 843, 1058, 1251, 1428, 1445, 1614, 1655, 2958.

Example 2

The procedures of Example 1 were repeated, except that the silicone compound prepared in Synthesis Example 2 was used in place of the silicone compound prepared in Synthesis Example 1, to obtain a pale yellow and transparent product which was oily at room temperature. A molecular structure of the product obtained was analyzed by ¹H-NMR and IR to find that the product was a silicone compound represented by the following formula. The yield was 89%.

The ¹H-NMR spectra and IR spectra are as described below.

¹H-NMR (400 MHz, CDCl₃): δ 0.09 (s, 27H), 0.41-0.50 (m, 2H), 0.85-0.92 (m, 3H), 1.20-1.32 (m, 2H), 1.12-1.50 (m, 4H), 3.20-3.31 (m, 2H), 3.32-3.39 (m, 2H), 5.62 (dd, J=10.3, 2.0 Hz, 1H), 6.31 (ddd, 16.7, 8.4, 2.0 Hz, 1H), 6.53 (dd, 16.7, 10.3 Hz, 1H)

IR (NaCl): ν 793, 843, 1058, 1251, 1428, 1444, 1615, 1654, 2958.

Example 3

The procedures of Example 1 were repeated, except that the silicone compound prepared in Synthesis Example 3 was used in place of the silicone compound prepared in Synthesis Example 1, to obtain a pale yellow and transparent product which was oily at room temperature. A molecular structure of the product obtained was analyzed by ¹H-NMR and IR to find that the product was a silicone compound represented by the following formula. The yield was 93%.

The ¹H-NMR spectra and IR spectra are as described below.

¹H-NMR (400 MHz, CDCl₃): δ 0.08 (s, 27H), 0.43-0.52 (m, 2H), 1.22-1.34 (m, 2H), 2.71-3.01 (m, 4H), 3.20-3.33 (m, 4H), 5.60 (dd, J=10.3, 2.0 Hz, 1H), 6.25 (ddd, 16.7, 8.4, 2.0 Hz, 1H), 6.46 (dd, 16.7, 10.3 Hz, 1H)

IR (NaCl): ν 792, 843, 1058, 1189, 1251, 1428, 1445, 1614, 1655, 2958.

Comparative Example 1

In a 100 mL three-necked flask equipped with a thermometer, a dropping funnel and a nitrogen inflow instrument, and a magnetic stirring bar therein, were put 1 mole of [(CH₃)₃SiO]₃Si(CH₂)₃NH₂, 1.05 moles of acrylic acid chloride and 2.0 moles of sodium carbonate in an aqueous 10% solution and stirred. Subsequently, the mixture was washed with water, filtrated through a paper filter and, then, volatile materials were distilled off under a reduced pressure to obtain a colorless product which was solid at room temperature and had a melting point of 51 degrees C. A molecular structure of the product obtained was analyzed by ¹H-NMR and IR to find that the product was a silicone compound represented by the following formula. The yield was 92%.

The $^1$H-NMR spectra and IR spectra are as described below.

$^1$H-NMR (400 MHz, CDCl$_3$): δ 0.09 (s, 27H), 0.45-0.50 (m, 2H), 1.59 (quin., J=7.0 Hz, 2H), 3.32 (q, J=7.0 Hz, 2H), 5.58 (brs, 1H), 5.62 (dd, J=10.3, 1.4 Hz, 1H), 6.06 (ddd, 17.0, 8.4, 1.4 Hz, 1H), 6.25 (dd, 17.0, 10.3 Hz, 1H)

IR (ATR): ν 753, 835, 1041, 1248, 1408, 1556, 1625, 1655, 2958, 3285.

The states of the silicone compounds prepared in Examples 1 to 3 and Comparative Example 1 at room temperature are summarized in the following Table 1.

TABLE 1

|  | Example 1 | Example 2 | Example 3 | Comparative Example |
|---|---|---|---|---|
| State at room temperature | Liquid | Liquid | Liquid | Solid |

The silicone compound prepared in Comparative Example 1 had a melting point of 51 degrees C. and was solid at room temperature. In contrast, the silicone compounds of the present invention were liquid at room temperature and had good handling properties.

INDUSTRIAL APPLICABILITY

The present silicone compound has a low melting point and is liquid at room temperature, so that the compound has good handling properties and good compatibility with other monomer. Therefore, the present silicone compound is useful for ophthalmic device compositions, coating materials and cosmetic compositions for a skin care, a hair care, an antiperspirant, a deodorant, a makeup or an ultraviolet protection.

The invention claimed is:

1. A silicone compound represented by the following general formula (1):

(1)

wherein $R^1$, $R^2$ and $R^3$ are, independently of each other, represented by the following formula (a):

(a)

wherein R is, independently of each other, a monovalent hydrocarbon group having 1 to 10 carbon atoms and n is an integer of from 0 to 20;

A is represented by the following formula (2) or (3):

(2)

wherein $R^c$ is an alkyl group having 1 to 10 carbon atoms and Z is a radical-polymerizable group;

(3)

wherein $p^1$ and $p^2$ are, independently of each other, positive integers such that a total number of $p^1$ and $p^2$ is 3 to 10, and Z is a radical-polymerizable group; and Q is a substituted or unsubstituted divalent hydrocarbon group having 1 to 10 carbon atoms.

2. The silicone compound according to claim 1, represented by the following general formula:

wherein A is a group selected from the following formulas:

wherein $R^c$ is a butyl, n-hexyl or cyclohexyl group and Z is a radical-polymerizable group.

3. The silicone compound according to claim 1, wherein the radical-polymerizable group is an acryl group or a methacryl group.

4. A method for preparing a silicone compound represented by the following general formula (1):

(1)

wherein $R^1$, $R^2$ and $R^3$ are, independently of each other, represented by the following formula (a):

(a)

wherein R is, independently of each other, a monovalent hydrocarbon group having 1 to 10 carbon atoms and n is an integer of from 0 to 20;

A is represented by the following formula (2) or (3):

(2)

wherein $R^c$ is an alkyl group having 1 to 10 carbon atoms and Z is a radical-polymerizable group;

(3)

wherein $p^1$ and $p^2$ are, independently of each other, positive integers such that a total number of $p^1$ and $p^2$ is 3 to 10, and Z is a radical-polymerizable group; and Q is a substituted or unsubstituted divalent hydrocarbon group having 1 to 10 carbon atoms;

wherein the method comprises a step of reacting a compound represented by the following formula (4):

(4)

wherein $R^1$, $R^2$, $R^3$ and Q are as defined above, X is a group selected from the group consisting of a chlorine atom, a bromine atom, a bromanyl group, an iodine atom, an iodanyl group, a mesyl group, a tosyl group, a trifluoromethanesulfonyl group, a nosyl group and an epoxy group;

with a compound represented by the following formula (5) or (6):

$R^c$—NH$_2$   (5)

(6)

wherein $R^c$, $p^1$ and $p^2$ are as defined above;

in a polar solvent and in the presence of a base and a reaction promoter to prepare a precursor compound represented by the following formula (1'):

(1')

wherein $R^1$, $R^2$, $R^3$ and Q are as defined above and A' is represented by the following formula (2') or (3'):

(2')

(3')

wherein $R^c$, $p^1$ and $p^2$ are as defined above;

and subsequently a step of reacting said precursor compound represented by the aforesaid formula (1') with a compound having a radical-polymerizable group to prepare the silicone compound represented by the aforesaid formula (1).

5. The method according to claim 4, wherein the compound having a radical-polymerizable group is (meth)acrylic acid chloride.

6. The method according to claim 4, wherein the compound represented by the aforesaid formula (6) is piperazine.

7. The method according to claim 4, wherein X in the aforesaid formula (4) is a chlorine atom.

8. The method according to claim 4, wherein the base is selected from alkali metal salts, alkaline earth metal salts and tertiary amine compounds.

9. The method according to claim 8, wherein the base is pyridine.

10. The method according to claim 4, wherein the reaction promoter is selected from the group consisting of lithium bromide, lithium iodide, sodium bromide, sodium iodide, quaternary alkylammonium bromide, quaternary ammonium iodide, potassium bromide and potassium iodide.

11. The method according to claim 10, wherein the reaction promoter is potassium iodide.

12. The method according to claim 4, wherein the polar solvent is at least one selected from the group consisting of amide compounds, ether compounds, keton compounds, alkyl nitrile compounds and halogenated hydrocarbon compounds.

* * * * *